(12) United States Patent
Meyer et al.

(10) Patent No.: US 7,655,624 B2
(45) Date of Patent: Feb. 2, 2010

(54) PEPTIDE AND PEPTIDE MIMETIC CONJUGATES WITH INTEGRIN-INHIBITOR PROPERTIES

(75) Inventors: Joerg Meyer, Heusenstamm (DE); Berthold Nies, Fraenkisch-Crumbach (DE); Michel Dard, Seeheim-Jugenheim (DE); Guenter Hoelzemann, Seeheim-Jugenheim (DE); Horst Kessler, Schwalbach (DE); Martin Kantlehner, Freising (DE); Ulrich Hersel, Erlabrunn (DE); Christoph Gibson, Ihringen (DE); Gabor Sulyok, Munich (DE)

(73) Assignee: Biomet Deutschland GmbH, Berlin (DE)

( * ) Notice: Subject to any disclaimer, the term of this patent is extended or adjusted under 35 U.S.C. 154(b) by 1415 days.

(21) Appl. No.: 10/344,669

(22) PCT Filed: Aug. 2, 2001

(86) PCT No.: PCT/EP01/08932

§ 371 (c)(1),
(2), (4) Date: Feb. 14, 2003

(87) PCT Pub. No.: WO02/13872

PCT Pub. Date: Feb. 21, 2002

(65) Prior Publication Data

US 2004/0029782 A1    Feb. 12, 2004

(30) Foreign Application Priority Data

Aug. 17, 2000 (DE) .............................. 100 40 105

(51) Int. Cl.
*A61K 38/12* (2006.01)
*A61F 2/02* (2006.01)

(52) U.S. Cl. ........................... 514/11; 530/317; 424/423

(58) Field of Classification Search ....................... None
See application file for complete search history.

(56) References Cited

U.S. PATENT DOCUMENTS

| 6,280,760 B1 | 8/2001 | Meyer et al. |
| 6,326,403 B1 | 12/2001 | Holzemann et al. |
| 6,610,826 B1 | 8/2003 | Meyer et al. |
| 6,649,613 B1 | 11/2003 | Holzemann et al. |

FOREIGN PATENT DOCUMENTS

| DE | 43 106 43 A1 | 10/1994 |
| DE | 197 55 800 A1 | 6/1999 |
| DE | 198 31 710 A1 | 1/2000 |
| DE | 19755801 | 6/2000 |
| DE | 199 32 796 A1 | 1/2001 |
| EP | 1 309 355 | 5/2003 |
| WO | WO 2007/062525 A1 | 6/2007 |

OTHER PUBLICATIONS

Kantlehner, 1999, Angew Chem Int. Ed., 38, 560-562.*
Trammell, et al., Inorganic Chemistry, 1999, vol. 38, No. 161, 3665-3669.*
Nakhle B M et al., "Synthesis of 3,5-bis(phosphonomethyl) benzoic acid and its application as a metal oxide surface bivalent anchor," Tetrahedron, Mar. 5, 1999, pp. 2835-2846, vol. 55, No. 10, XP004157121, ISSN: 0040-4020, the entire document, Elsevier Science Publishers, Amsterdam, NL.
Chu et al., "Presentation of Ligands on Hydroxylapatite," Bioconjugate Chemistry, 1997, pp. 103-105, vol. 8, No. 2, XP002073553, ISSN: 1043-1802, p. 104, American Chemical Society, Washington, US.
J.W. Smith et al, "J. Biol. Chem.", 1990, vol. 265, pp. 12267-12271.
P. C. Brooks et al., "Science", 1994, vol. 264, pp. 569-571.
P. C. Brooks et al., "Cell", 1994, vol. 79, pp. 1157-1164.
P. Valentin-Weigand et al., "Infection and Immunity", 1988, pp. 2851-2855.
R. Keenan et al., "Abstr. Pap. 211th ACS National Meeting", 1996.
Houben-Weyl, L.C., vol. 15/11, 1974, pp. 1-806.
S. Zimmer et al., Liebigs Ann. Chem., 1993, pp. 497-501.
R. B. Merrifield et al., 1985, vol. 97, pp. 801-812.
B.F. Gysin et al., J. Am. Chem. Soc., 1972, vol. 94, pp. 3012.
G. B. Fields et al., Int. J. Pept. Protein Res., 1990, vol. 35, pp. 161-214.
Gilbert et al., "Journal of Biological Chemistry", 2000, vol. 275, No. 21, pp. 16213-16218.

* cited by examiner

*Primary Examiner*—Andrew D Kosar
*Assistant Examiner*—Satyanarayana R Gudibande
(74) *Attorney, Agent, or Firm*—Millen, White, Zelano, Branigan, P.C.

(57) ABSTRACT

The invention relates to compounds of formula (1) B-Q-$X_1$, wherein B is bioactive cell adhesive mediating molecule. Q is absent or is an inorganic spacer molecule and $X_1$ is an anchor molecule, selected from the group Lys-(CO—$CH_2$—$(CH_2)_n$—$PO_3H_2)_2$(I), -Lys-[-Lys-(CO—$CH_2$—$(CH_2)_a$—$PO_3H_2)_2]_2$(ii) or -Lys-(Lys[-Lys-(CO—$CH_2$—$(CH_2)_n$—$PO_3H_2]_2$ (iii), and n independently represents 0, 1, 2 or 3, wherein a free amino group of group B is linked in peptide form to a free carboxyl group of the spacer molecule Q or of the anchor molecule $X_1$, or a free amino group of the radical Q is linked in peptide form to a free carboxyl group of the radical $X_1$. The invention also relates to the salts thereof. The inventive compounds can be used as integrin inhibitors for the treatment of illnesses, deficiencies, inflammations caused by implants and osteolytic illnesses such as osteoporosis, thrombosis, cardiac infarction and arteriosclerosis, in addition to the acceleration and strengthening of the integration process of implants or the biocompatible surface in tissue.

12 Claims, No Drawings

SEQUENCE LISTING

```
<160> NUMBER OF SEQ ID NOS: 6

<210> SEQ ID NO 1
<211> LENGTH: 12
<212> TYPE: PRT
<213> ORGANISM: Artificial Sequence
<220> FEATURE:
<223> OTHER INFORMATION: Synthetic construct

<400> SEQUENCE: 1

Thr Trp Tyr Lys Ile Ala Phe Gln Arg Asn Arg Lys
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic construct

<400> SEQUENCE: 2

Trp Tyr Lys Ile Ala Phe Gln Arg Asn Arg Lys
1               5                   10
```

```
<210> SEQ ID NO 3
<211> LENGTH: 10
<212> TYPE: PRT
<213> ORGANISM: Artificial Sequence
<220> FEATURE:
<223> OTHER INFORMATION: Synthetic construct

<400> SEQUENCE: 3

Tyr Lys Ile Ala Phe Gln Arg Asn Arg Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic construct

<400> SEQUENCE: 4

Thr Trp Tyr Lys Ile Ala Phe Gln Arg Asn Arg
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic construct

<400> SEQUENCE: 5

Thr Trp Tyr Lys Ile Ala Phe Gln Arg Asn
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic construct

<400> SEQUENCE: 6

Thr Trp Tyr Lys Ile Ala Phe Gln Arg
1               5
```

PEPTIDE AND PEPTIDE MIMETIC CONJUGATES WITH INTEGRIN-INHIBITOR PROPERTIES

This application is a National Stage application under §371 of PCT/EP01/08932, filed Feb. 14, 2003, and claims priority to DE 10040105.8 filed Aug. 17, 2000.

The invention relates to compounds of the formula I $$B-Q-X_1 \qquad \qquad I$$

in which
B is a bioactive, cell adhesion-mediating molecule
Q is absent or is an organic spacer molecule and
$X_1$ is an anchor molecule selected from the group $$\text{-Lys-(CO—CH}_2\text{—(CH}_2)_n\text{—PO}_3\text{H}_2)_2 \qquad (i)$$

$$\text{-Lys-[Lys-(CO—CH}_2\text{—(CH}_2)_n\text{—PO}_3\text{H}_2)_2]_2 \qquad (ii) \text{ or}$$

$$\text{-Lys-(Lys[-Lys-(CO—CH}_2\text{—(CH}_2)_n\text{—PO}_3\text{H}_2)_2]_2)_2 \qquad (iii),$$

and n, in each case independently of one another, is 0, 1, 2 or 3 and where a free amino group of the group B and a free carboxyl group of the spacer molecule Q or of the anchor molecule $X_1$ or a free amino group of the radical Q and a free carboxyl group of the radical $X_1$ are linked to one another like peptides, and their salts.

Similar compounds are disclosed in DE 19932796, DE 19755800 and DE 19831710.

The invention was based on the object of finding novel compounds having valuable properties, in particular those which can be used for the production of medicaments.

It has been found that the compounds of the formula I and their salts have very valuable pharmacological properties, together with good tolerability. They act especially as integrin inhibitors, inhibiting, in particular, the interactions of the $\alpha_v\beta_3$ or $\alpha_v\beta_5$ integrin receptors with ligands, e.g. the binding of fibrinogen to the $\beta_3$ integrin receptor. The compounds show particular activity in the case of the integrins $\beta_v\beta_3$, $\alpha_v\beta_5$, $\alpha_{IIb}\beta_3$, $\alpha_v\beta_1$, $\alpha_v\beta_6$ and $\alpha_v\beta_8$.

This action can be demonstrated, for example, according to the method which is described by J. W. Smith et al. in J. Biol. Chem. 265, 12267-12271 (1990).

The dependence of the development of angiogenesis on the interaction between vascular integrins and extra-cellular matrix proteins is described by P. C. Brooks, R. A. Clark and D. A. Cheresh in Science 264, 569-71 (1994).

The possibility of inhibiting this interaction and thereby inducing apoptosis (programmed cell death) of angiogenic vascular cells by means of a cyclic peptide is described by P. C. Brooks, A. M. Montgomery, M. Rosenfeld, R. A. Reisfeld, T.-Hu, G. Klier and D. A. Cheresh in Cell 79, 1157-64 (1994).

Compounds of the formula I which block the interaction of integrin receptors and ligands, e.g. of fibrinogen to the fibrinogen receptor (glycoprotein IIb/IIIa), prevent, as GPIIb/IIIa antagonists, the spread of tumour cells by metastasis. This is confirmed by the following observations:

the spread of tumour cells from a local tumour into the vascular system takes place through the formation of microaggregates (microthrombi) by interaction of the tumour cells with blood platelets. The tumour cells are screened by the protection in the microaggregate and are not recognized by the cells of the immune system. The microaggregates can attach to vessel walls, owing to which further penetration of tumour cells into the tissue is facilitated.

Since the formation of the microthrombi is mediated by fibrinogen binding to the fibrinogen receptors on activated blood platelets, the GPIIa/IIIb antagonists can be regarded as effective metastasis inhibitors.

The phosphonate radical serves to bind the peptides ionically or adsorptively to biocompatible surfaces of, for example, implants which contain the oxides, e.g. metal surfaces (e.g. titanium or titanium alloys such as $TiAl_6V_4$) or cation-containing surfaces, e.g. on amorphous or sintered calcium phosphate (e.g. hydroxy-apatite, bones, teeth) or calcium phosphate cements (e.g. Biocement D).

The invention therefore relates in particular to the compounds of the formula I for ionic or adsorptive binding via the functional group of the radical $X_1$ to biocompatible surfaces.

The peptides according to the invention now make possible the biofunctionalization of biomaterials, in particular implants for human and animal organs, by means of coating thereof, mainly the adhesion of those cell species being stimulated which should in each case effect the tissue integration of the corresponding biomaterial. Using such coatings, an accelerated and enhanced integration of various biomaterials/implants with improved long-term stability after their incorporation into the body can be achieved.

The peptides according to the invention bind selectively to integrins. After immobilization on biocompatible surfaces, e.g. implants, they stimulate the adhesion of cells which carry integrins.

After coating of the compounds on the surfaces, those cell species can selectively be stimulated to binding which should also effect the implant integration after implantation in the natural tissue. In osteoblasts, osteoclasts and endothelial cells these are, for example, $\alpha_v$-carrying cell species.

The invention therefore relates to the compounds of the formula I as integrin inhibitors for selective cell enrichment in implants.

After anchoring to a biocompatible surface as pharmaceutical active compounds, the compounds of the formula I can be employed in human and veterinary medicine, in particular they can be employed as integrin inhibitors for the treatment of disorders, defects and inflammations caused by implants, such as inadequate and delayed integration of biomaterials and implants, of thrombosis caused by implants, of bone and tooth defects, and of osteolytic disorders such as osteoporosis, thrombosis, cardiac infarct, arteriosclerosis, in wound healing for assisting the healing process, and also for the acceleration and strengthening of the integration process of the implant or of the biocompatible surface into the tissue.

The compounds of the formula I can be employed as substances having antimicrobial action in operations where biomaterials, implants, catheters or cardiac pacemakers are used. They have an antiseptic action here. The efficacy of the antimicrobial activity can be demonstrated by the procedure described by P. Valentin-Weigund et al., in Infection and Immunity, 2851-2855 (1988).

The invention thus relates to the compounds of the formula I as integrin inhibitors for the treatment of disorders, defects and inflammations caused by implants, and of osteolytic disorders such as osteoporosis, thrombosis, cardiac infarct and arteriosclerosis, and also for the acceleration and strengthening of the integration process of the implant or of the biocompatible surface into the tissue.

The invention further relates to the use of compounds of the formula I for the production of a medicament for the treatment of disorders, defects and inflammations caused by implants, and of osteolytic disorders such as osteoporosis, thrombosis, cardiac infarct and arteriosclerosis, and for the acceleration and strengthening of the integration process of the implant or of the biocompatible surface into the tissue.

Corresponding peptides carrying phosphonate anchors can be bonded ionically to carriers with oxide-containing surfaces, such as implants, affinity chromatography materials, or microtitre plates or else to cation-containing surfaces such as on amorphous or sintered calcium phosphates (e.g. hydroxyapatite, bones, teeth) or calcium phosphate cements (e.g. Biocement D).

The invention also relates to the use of compounds of the formula I for the coating, by means of ionic or adsorptive binding, of implants for human and animal organs.

The abbreviations of amino acid residues mentioned above and below stand for the radicals of the following amino acids:

| | |
|---|---|
| Abu | 4-aminobutyric acid |
| Aha | 6-aminohexanoic acid, 6-aminocaproic acid |
| Ala | alanine |
| Asn | asparagine |
| Asp | aspartic acid |
| Arg | arginine |
| Cys | cysteine |
| Dab | 2,4-diaminobutyric acid |
| Dap | 2,3-diaminopropionic acid |
| Gln | glutamine |
| Glp | pyroglutamic acid |
| Glu | glutamic acid |
| Gly | glycine |
| His | histidine |
| homo-Phe | homo-phenylalanine |
| Ile | isoleucine |
| Leu | leucine |
| Lys | lysine |
| Met | methionine |
| Nle | norleucine |
| Orn | ornithine |
| Phe | phenylalanine |
| Phg | phenylglycine |
| 4-Hal-Phe | 4-halophenylalanine |
| Pro | proline |
| Ser | serine |
| Thr | threonine |
| Trp | tryptophan |
| Tyr | tyrosine |
| Val | valine. |

In addition, the abbreviations below have the meanings:

| | |
|---|---|
| Ac | acetyl |
| BOC | tert-butoxycarbonyl |
| CBZ or Z | benzyloxycarbonyl |
| DCCI | dicyclohexylcarbodiimide |
| DMF | dimethylformamide |
| EDCI | N-ethyl-N,N'-(dimethylaminopropyl)carbodiimide |
| Et | ethyl |
| FCA | fluoresceincarboxylic acid |
| FITC | fluorescein isothiocyanate |
| Fmoc | 9-fluorenylmethoxycarbonyl |
| FTH | fluoresceinthiourea |
| HOBt | 1-hydroxybenzotriazole |
| Me | methyl |
| MBHA | 4-methylbenzhydrylamine |
| Mtr | 4-methoxy-2,3,6-trimethylphenylsulfonyl |
| HATU | O-(7-azabenzotriazol-1-yl)-N,N,N',N'-tetramethyluronium hexafluorophosphate |
| HONSu | N-hydroxysuccinimide |
| OtBu | tert-butyl ester |
| Oct | octanoyl |
| OMe | methyl ester |
| OEt | ethyl ester |
| POA | phenoxyacetyl |
| Pbf | pentamethylbenzofuranyl |
| Pmc | 2,2,5,7,8-pentamethylchroman-6-sulfonyl |
| Sal | salicyloyl |

| | |
|---|---|
| Su | succinyl |
| TIPS | triisopropylsilane |
| TFA | trifluoroacetic acid |
| TMSBr | trimethylsilyl bromide |
| Trt | trityl (triphenylmethyl). |

If the abovementioned amino acids can occur in a number of enantiomeric forms, all these forms and their mixtures (e.g. the DL forms) are included above and below, e.g. as part of the compounds of the formula I. In addition, the amino acids, e.g. as part of compounds of the formula I, can be provided with corresponding protective groups which are known per se.

Above all, side chain modifications of arginine, such as were carried out, for example, in the case of the non-peptide $\alpha_v\beta_3$ antagonists (e.g. by R. Keenan et al., Abstr. Pap. 211th ACS National Meeting (New Orleans, USA) 1996, MEDI 236), can also be employed in the case of the cyclopeptides, e.g. benzimidazole derivatives instead of the guanidine group.

"Prodrug derivatives" are also included in the compounds according to the invention, i.e. compounds of the formula I modified with, for example, alkyl or acyl groups, sugars or oligopeptides, which are rapidly cleaved in the body to give the active compounds according to the invention.

The invention further relates to an implant which is suitable for human and animal organs, consisting of a carrier matrix and a layer of a bioactive, cell adhesion-mediating molecule surrounding this matrix, the surrounding layer being formed from a compound of the formula I, and an ionic or adsorptive bond being present between carrier matrix and this compound.

Preferably, the carrier matrix and/or its surface consists of a metal or metal oxide. Particularly preferably, the carrier matrix and/or its surface consists of a bone or tooth substitute material, e.g. of calcium phosphate mixtures.

The invention further relates to a process for the preparation of compounds of the formula I according to claim 1, and of their salts, characterized in that a bioactive molecule B, which can be provided with protective groups, and a spacer-anchor molecule (Q-$X_1$) or anchor molecule ($X_1$) provided with protective groups are linked to one another in peptide fashion and the protective groups are then removed, and/or in that a basic or acidic compound of the formula 1 [sic] is converted into one of its salts by treating with an acid or base.

Above and below, the radicals B, Q and $X_1$ have the meaning indicated under the formula I, if not expressly stated otherwise.

B is preferably a cyclo(Arg-Gly-Asp-$Z_1$)-,

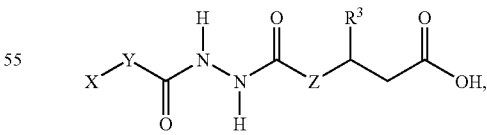

Thr-Trp-Tyr-Lys-Ile-Ala-Phe-Gln-Arg-Asn-Arg-Lys-, (SEQ. ID. NO. 1),

Trp-Tyr-Lys-Ile-Ala-Phe-Gln-Arg-Asn-Arg-Lys-, (SEQ. ID. NO. 2),

Tyr-Lys-Ile-Ala-Phe-Gln-Arg-Asn-Arg-Lys-, (SEQ. ID. NO. 3),

Thr-Trp-Tyr-Lys-Ile-Ala-Phe-Gln-Arg-Asn-Arg-, (SEQ. ID. NO. 4),

Thr-Trp-Tyr-Lys-Ile-Ala-Phe-Gln-Arg-Asn- (SEQ. ID. NO. 5) or a
Thr-Trp-Tyr-Lys-Ile-Ala-Phe-Gln-Arg- residue, (SEQ. ID. NO. 6), where $Z_1$, is in each case, independently of one another, an amino acid residue or a di- or tripeptide residue, where the amino acids are selected, independently of one another, from the group consisting of Ala, Asn, Asp, Arg, Cys, Gln, Glu, Gly, His, Homo-Phe, Ile, Leu, Lys, Orn, Met, Phe, Phg, Pro, Ser, Thr, Trp, Tyr, Val.

Q is absent or is an organic spacer molecule. Preferably, this is a [CO—$(CH_2)_x$—NH—$]_m$—, [CO—$CH_2$(O—$CH_2CH_2)_y$—NH—$]_m$—, [CO—$(CH_2)_z$—CO]—, [NH—$(CH_2)_z$—NH—]—, [CO—$CH_2$—$(OCH_2CH_2)_y$—O—$CH_2$—CO—]— or an [NH—$CH_2CH_2$—$(OCH_2CH_2)_y$—NH—]— radical, and their combinations, where the ranges of values claimed in claim 3 apply to the indices m, x, y and z. The abovementioned compounds which can assume values between 1 and 8 for m, values between 1 and 5 for x and values between 1 and 6 for y and z have proved particularly advantageous.

$X_1$ is an anchor molecule, preferably from the group -Lys-(CO—$CH_2$—$(CH_2)_n$—$PO_3H_2)_2$, -Lys-[Lys-(CO—$CH_2$—$(CH_2)_n$—$PO_3H_2)_2]_2$ or -Lys-(Lys[-Lys-(CO—$CH_2$—$(CH_2)_n$—$PO_3H_2)_2]_2)_2$, where n can in case independently of one another be 0, 1, 2, or 3.

The amino acids and amino acid residues mentioned in the meanings for $Z_1$ may also be derivatized, with N-methyl, N-ethyl, N-propyl, N-benzyl or $C_\alpha$-methyl derivatives being preferred. Also preferred are derivatives of Asp and Glu, especially the methyl, ethyl, propyl, butyl, tert-butyl, neopentyl or benzyl esters of the side-chain carboxyl groups, as well as derivatives of Arg, which may be substituted on the —NH—C(=NH)—$NH_2$ group by an acetyl, benzoyl, methoxy-carbonyl or ethoxycarbonyl radical.

X is preferably $H_2N$—C(=NH)—NH—, Het-NH—, $H_2N$—C(=NH)—, A-C(=NH)—NH or a Het radical.

Y is preferably —$(CH_2)_n$— or

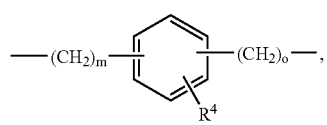

—$(CH_2)_s$—CH($R^4$)—$(CH_2)_t$— or —$(CH_2)_p$-$Het^1$-$(CH_2)_q$— radical.

Z is preferably N—$R^2$ or CH—$R^2$, where $R^2$ can preferably be an H atom or alkyl radical having 1 to 4 C atoms.

$R^3$ is preferably an H atom, Ar, Het or A radical, where A, Ar and Het have one of the meanings indicated previously or below.

$R^4$ is preferably an H atom, A, Ar, OH, OA, OAr, arylalkyl, Hal, CN, $NO_2$ $CF_3$ or $OCF_3$ radical. Arylalkyl is preferably benzyl, phenylethyl, phenylpropyl or naphthylmethyl, particularly preferably benzyl.

A is preferably a COOH, $NH_2$ or alkyl radical having 1 to 6 C atoms, which is unsubstituted or substituted by COOH or $NH_2$. A is preferably methyl, furthermore ethyl, propyl, n-butyl, isobutyl, sec-butyl or tert-butyl, in addition also n-pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. A is particularly preferably methyl.

Ar is preferably phenyl which is unsubstituted or mono-, di- or trisubstituted by A, OH, OA, $CF_3$, $OCF_3$, CN, $NO_2$ or Hal, which can be substituted by phenyl which is mono-, di- or trisubstituted by A, OH, OA, $NH_2$, $OCF_3$, CN, $NO_2$ or Hal in such a way that an unsubstituted or substituted biphenyl results.

Ar is therefore preferably phenyl, o-, m- or p-methyl-phenyl, o-, m- or p-ethylphenyl, o-, m- or p-propyl-phenyl, o-, m- or p-isopropylphenyl, o-, m- or p-tert-butylphenyl, o-, m- or p-hydroxyphenyl, o-, m- or p-methoxyphenyl, o-, m- or p-ethoxyphenyl, o-, m-, p-trifluoromethylphenyl, o-, m-, p-trifluoromethoxy-phenyl, o-, m- or p-fluorophenyl, o-, m- or p-chloro-phenyl, o-, m- or p-bromophenyl, o-, m-. p-nitrophenyl, o-, m- or p-aminomethylphenyl.

Het is a saturated, partly or completely unsaturated mono- or bicyclic heterocyclic radical having 5 to 10 ring members, where 1 to 3 N and/or 1 S or O atom(s) can be present and the heterocyclic radical can be mono- or disubstituted by CN, Hal, OH, $NH_2$, COOH, OA, $CF_3$, A, $NO_2$, Ar or $OCF_3$.

Het is preferably an o-, m- or p-substituted pyridyl, a 2-, 4-, 5- or 6-substituted pyrimidyl or a 3-, 4-, 5- or 6-substituted pyridazyl which is preferably unsubstituted or substituted by a methyl, ethyl or propyl group or a methylamino, ethylamino or propylamino group [relates to all of the three heteroaromatics mentioned], and also a 2-substituted benzimidazolyl which is unsubstituted or substituted by a 3-methyl, 3-ethyl or 3-benzyl group, and also a 2-substituted dihydroimidazolyl, tetrahydropyrimidyl or tetrahydro-pyridyl.

Examples which are preferably contained in Het are:

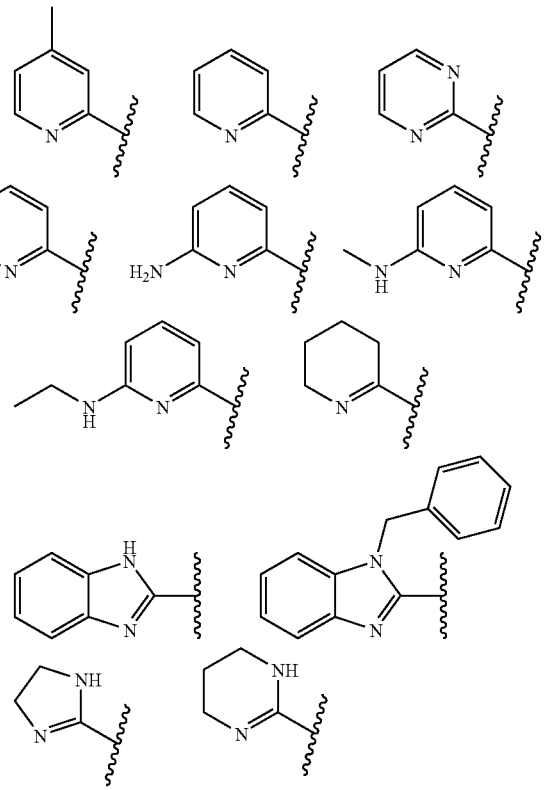

$Het^1$ is a 5- or 6-membered aromatic heterocycle having 1 to 4 N, O and/or S atoms, which can be unsubstituted or mono- or disubstituted by F, Cl, Br, A, OA or $OCF_3$.

Het¹ is preferably a 2,4-, 3,5- or 2,5-disubstituted pyridyl or a 2,4-, 2,5-, 2,6- or 4,6-disubstituted pyrimidyl, a 2,4- or 2,5-disubstituted 1,3-oxazolyl or 1,3-thiazolyl.

OA is preferably methoxy, ethoxy, propoxy or butoxy, in addition also pentyloxy or hexyloxy.

Hal is preferably F, Cl or Br, but also I.

The indices n, m, o, p, q, s and t have the meaning indicated in claim 2, if not expressly stated otherwise.

The compounds of the formula I can have one or more chiral centres and therefore occur in various stereo-isomeric forms. The formula I includes all these forms.

Accordingly, the invention relates in particular to those compounds of the formula I in which at least one of the radicals mentioned has one of the preferred meanings indicated above.

Particularly preferred compounds of the formula I are the following:
a) Cyclo-(Arg-Gly-Asp-D-Phe-Lys($N^\epsilon$H—[CO—$(CH_2)_5$—NH]$_2$-Lys-[Lys-(CO—$CH_2$—$(CH_2)_n$—$PO_3H_2)_2]_2$));
b) Cyclo-(Arg-Gly-Asp-D-Phe-Lys($N^\epsilon$H—[CO—$(CH_2)_5$—NH]$_3$-Lys-[Lys-(CO—$CH_2$—$(CH_2)_n$—$PO_3H_2)_2]_2$));
c) Cyclo-(Arg-Gly-Asp-D-Phe-Lys($N^\epsilon$H—[CO—$CH_2$(—O—$CH_2CH_2)_6$—NH]$_2$-Lys-[Lys-(CO—$CH_2$—$(CH_2)_n$—$PO_3H_2)_2]_2$));

where n is 1.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart;) namely under reaction conditions which are known and suitable for the reactions mentioned. Use can also be made in this case of variants which are known per se, but not mentioned here in greater detail.

If desired, the starting substances can also be formed in situ such that they are not isolated from the reaction mixture, but immediately reacted further to give the compounds of the formula I.

The fragment coupling or the coupling between ligand and linker is generally carried out in an inert solvent, a carboxylic acid fragment (phosphonate linker, e.g. HO—[CO—$(CH_2)_5$—NH]$_2$-Lys-[Lys-(CO—$CH_2$—$CH_2$—$PO_3(C_2H_5)_2)_2]_2$) being dissolved in DMF with HATU, HOAt and 2,4,6-collidine and treated with an amine fragment (cyclopeptide, e.g. c[R(Pbf)G(OtBu)fK]).

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, N-methylpyrrolidone, dimethylacetamide or dimethylformamide (DMF); nitriles such as acetonitrile; sulfoxides such as dimethyl sulfoxide (DMSO), carbon disulfide; carboxylic acids such as formic acid or acetic acid; nitro compounds such as nitromethane or nitrobenzene; esters such as ethyl acetate, water or mixtures of the solvents mentioned.

Cyclic compounds can be prepared by cyclization of the linear compounds, such as described, for example, in DE 43 10 643, in Houben-Weyl, l.c., Volume 15/II, pages 1 to 806 (1974) or by S. Zimmer, E. Hoffmann, G. Jung and H. Kessler, Liebig's Ann. Chem. 1993, 497-501.

The linear peptides can be synthesized, for example, according to R. B. Merrifield, Angew. Chemie 1985, 97, 801-812.

Open-chain linear compounds, such as, for example, compounds of the formula I can otherwise be prepared by customary methods of amino acid and peptide synthesis, e.g. also by the solid-phase synthesis according to Merrifield (see also, for example, B. F. Gysin and R. B. Merrifield, J. Am. Chem. Soc. 94, 3012 ff. (1972)).

The compounds of the formula I can furthermore be obtained by liberating them from their functional derivatives by solvolysis, in particular hydrolysis, or by hydrogenolysis.

Preferred starting substances for the solvolysis or hydrogenolysis are those which, instead of one or more free amino and/or hydroxyl groups, contain corresponding protected amino and/or hydroxyl groups, preferably those, which instead of an H atom which is bonded to an N atom, carry an amino protective group, e.g. those which correspond to the formula I, but instead of an $NH_2$ group contain an NHR' group (in which R' is an amino protective group, e.g. BOC or CBZ).

Starting substances are furthermore preferred which, instead of the H atom of a hydroxyl group, carry a hydroxyl protective group, e.g. those which correspond to the formula I, but instead of a hydroxyphenyl group contain an R"O—phenyl group (in which R" is a hydroxyl protective group).

A number of—identical or different—protected amino and/or hydroxyl groups can also be present in the molecule of the starting substance. If the protective groups present are different from one another, in many cases they can be removed selectively.

The expression "amino protective group" is generally known and relates to groups which are suitable for protecting (for blocking) an amino group from chemical reactions, but which are easily removable after the desired chemical reaction has been carried out at other positions in the molecule. Typical groups of this type are, in particular, unsubstituted or substituted acyl, aryl, aralkoxymethyl or aralkyl groups. Since the protective groups are removed after the desired reaction (or reaction sequence), their nature and size is otherwise uncritical; preferably, however, those having 1-20, in particular 1-8, C atoms are preferred. The expression "acyl group" is to be interpreted in the widest sense in connection with the present process. It includes acyl groups derived from aliphatic, araliphatic, aromatic or heterocyclic carboxylic acids or sulfonic acids and also, in particular, alkoxycarbonyl, aryloxycarbonyland especially aralkoxycarbonylgroups. Examples of acylgroups of this type are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC, 2-iodoethoxycarbonyl; aralkyloxycarbonyl such as CBZ ("carbobenzoxy"), 4-methoxy-benzyloxycarbonyl, FMOC; arylsulfonyl such as Mtr Pbf or Pmc. Preferred amino protective groups are BOC and Mtr, additionally CBZ, Fmoc, benzyl and acetyl.

The expression "hydroxyl protective group" is likewise generally known and relates to groups which are suitable for protecting a hydroxyl group from chemical reactions, but which are easily removable after the desired chemical reaction has been carried out at other positions in the molecule. Typical groups of this type are the abovementioned unsubstituted or substituted aryl, aralkyl or acyl groups and additionally also alkyl groups. The nature and size of the hydroxyl protective groups is not critical, since they are removed again after the desired chemical reaction or reaction sequence; groups containing 1-20, in particular 1-10, C atoms are preferred. Examples of hydroxyl protective groups are, inter alia, benzyl, p-nitro-benzyl, p-toluenesulfonyl, tert-butyl and acetyl, benzyl and tert-butyl being particularly preferred. The COOH groups in aspartic acid and glutamic acid are preferably protected in the form of their tert-butyl esters (e.g. Asp (OtBu)).

The liberation of the compounds of the formula I from their functional derivatives is carried out—depending on the protective group used—, for example using strong acids, expediently using TFA or perchloric acid, but also using other strong inorganic acids such as hydrochloric acid or sulfuric acid, strong organic carboxylic acids such as trichloroacetic acid or sulfonic acids such as benzene- or p-toluenesulfonic acid. The presence of an additiona inert solvent is possible, but not always necessary. Suitable inert solvents are preferably organic solvents, for example carboxylic acids such as acetic acid, ethers such as tetrahydrofuran or dioxane, amides such as DMF, halogenated hydrocarbons such as dichloromethane, additionally also alcohols such as methanol, ethanol or isopropanol, and also water. Mixtures of the abovementioned solvents are additionally suitable. TFA is preferably used in an excess without addition of a further solvent, perchloric acid in the form of a mixture of acetic acid and 70% perchloric acid in the ratio 9:1. The reaction temperatures for the cleavage are expediently between approximately 0 and approximately 50°, the reaction is preferably carried out between 15 and 30° (room temperature).

The groups BOC, OtBu and Mtr can be removed, for example, preferably using TFA in dichloromethane or using approximately 3 to 5 N HCl in dioxane at 15-30°, the FMOC group using an approximately 5 to 50% solution of dimethylamine, diethylamine or piperidine in DMF at 15-30°.

The trityl group is employed for the protection of the amino acids histidine, asparagine, glutamine and cysteine. Removal is carried out, depending on the desired final product, using TFA/10% thiophenol, the trityl group being removed from all the abovementioned amino acids, when using TFA/anisole, TFA/thioanisole or TFA/TIPS/$H_2O$ the trityl group only being removed from His, Asn and. Gln, compared to which that on the Cys side chain remains.

The Pbf (pentamethylbenzofuranyl) group is employed for the protection of Arg. Removal is carried out, for example, using TFA in dichloromethane.

Hydrogenolytically removable protective groups (e.g. CBZ or benzyl) can be removed, for example, by treating with hydrogen in the presence of a catalyst (e.g. of a noble metal catalyst such as palladium, expediently on a support such as carbon). Suitable solvents in this case are those indicated above, in particular, for example, alcohols such as methanol or ethanol or amides such as DMF. As a rule, the hydrogenolysis is carried out at temperatures between approximately 0 and 100° and pressures between approximately 1 and 200 bar, preferably at 10-30° and 1-10 bar. Hydrogenolysis of the CBZ group is readily carried out, for example, on 5 to 10% Pd/C in methanol or using ammonium formate (instead of hydrogen) on Pd/C in methanol/DMF at 10-30°.

A base of the formula I can be converted into the associated acid addition salt using an acid, for example by reaction of equivalent amounts of the base and of the acid in an inert solvent such as ethanol and subsequent evaporation. Possible acids for this reaction are in particular those which give physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, additionally organic acids, in particular aliphatic, alicyclic, aralphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphtha- lenemono- and -disulfonic acids, and laurylsulfuric acid. Salts with physiologically unacceptable acids, e.g. picrates, can be used for the isolation and/or purification of the compounds of the formula I.

On the other hand, an acid of the formula I can be converted into one of its physiologically acceptable metal or ammonium salts by reaction with a base. Suitable salts in this case are in particular the sodium, potassium, magnesium, calcium and ammonium salts, additionally substituted ammonium salts, e.g. the dimethyl-, diethyl- or diisopropylammonium salts, monoethanol-, diethanol- or diisopropylammonium salts, cyclohexyl- or dicyclohexylammonium salts, dibenzylethylenediammonium salts, furthermore, for example, salts with arginine or lysine.

Above and below, all temperatures are indicated in ° C. In the following examples "customary working up" means: if necessary, water is added, the mixture is adjusted, if necessary, depending on the constitution of the final product, to a pH of between 2 and 10 and extracted with ethyl acetate or dichloromethane, the organic phase is separated off, dried over sodium sulfate and evaporated, and the residue is purified by chromatography on silica gel and/or by crystallization. $R_f$ values on silica gel: eluent: ethyl acetate/methanol 9:1.

RT=Retention time (minutes) on HPLC in the following systems:

| [A] | |
|---|---|
| Column: | YMC ODS A RP 5$C_{18}$, 250 × 4.6 mm |
| Eluent A: | 0.1% TFA in water |
| Eluent B: | 0.1% TFA in acetonitrile |
| Flow rate: | 1 ml/min |
| Gradient: | 0-50% B/30 min. |
| [B] | |
| as [A]; | |
| Gradient: | 5-50% B/30 min. |
| [C] | |
| as [A]; | |
| Gradient: | 10-50% B/30 min. |

Mass Spectrometry (MS):
 EI (electron impact ionization) $M^+$
 FAB (Fast Atom Bombardment) $(M+H)^+$
 ESI (Electrospray ionization) $(M+H)^+$ DMPP resin stands for 4-(2',4'-dimethoxyphenylhydroxymethyl)phenoxy resin, which allows, for example, the synthesis of side chain-protected peptides; TCP resin means trityl chloride-polystyrene resin.

The following examples describe on the one hand the fragment coupling and the cleavage of phosphonic esters, and the other hand the synthesis of selected cyclopeptide derivatives with phosphonate linker. The process for coating the various shaped articles made of metal or bone substitute materials is explained in detail by means of Examples 7 to 9.

EXAMPLE 1

Fragment Coupling in Solution 0.2 mmol of carboxylic acid fragment (phosphonate linker, e.g. HO—[CO—(CH$_2$)$_5$—NH]$_2$-Lys-[Lys-(CO—CH$_2$—CH$_2$—PO$_3$(C$_2$H$_5$)$_2$)$_2$]$_2$), 0.98 eq of HATU, 1.1 eq of HOAt and 10 eq of 2,4,6-collidine are dissolved in 2 ml of DMF. After 1.5 h, 1 eq of amine fragment (cyclopeptide, e.g. c[R(Pbf)G(OtBu)fK]) is added. The mixture is left to stir at room temperature for 24 h, and the product is purified by preparative HPLC.

EXAMPLE 2

Cleavage of Phosphonic Esters at the Phosphonate Linkers

The peptide with phosphonic ester groups is dissolved or, where apropriate, suspended in an ultrasonic bath in a 10:1 mixture of abs. CHCl$_3$ and TMSBr. After stirring for 3 days and, where appropriate, occasional slurrying of the precipitate in an ultrasound bath, the solvent is distilled off. The residue is lyophilized from H$_2$O.

The acidic side-chain protective groups are removed by conventional techniques.

EXAMPLE 3

Synthesis of the Phosphonate Linkers

The phosphonate linkers were synthesized in a solid-phase peptide synthesis according to the Fmoc strategy (see G. B. Fields, R. L. Nobie, Int. J. Pept. Protein Res. 1990, 35, 161-214).

The last building block coupled was 3-diethylphosphonopropionic acid.

Synthesis of 3-diethylphosphonopropionic Acid:

Benzyl 3-bromopropionate 58.3 mmol of 3-bromopropionyl chloride (10.0 g) and 1 eq of benzyl alcohol (6.3 g) are dissolved in 100 ml of dry DCM with stirring in a 250 ml round-bottomed flask with calcium chloride tube. After 2 days, 200 ml of CHCl$_3$ are added to the mixture, and the organic phase is extracted twice with saturated NaHCO$_3$ solution. After drying over MgSO$_4$, the solvent is distilled off, and the product is obtained as a colourless liquid.

Yield: 13.8 g (56.8 mmol, 97%) R$_f$=0.75 (H:EA 1:1). NMR (CDCl$_3$): $^1$H (250 MHz): δ=7.35 (s, 5H; H ar), 5.16 (s, 2H; CH$_2$—OCO), 3.58 (t, $^3$J(H,H)=7 Hz, 2H; CH$_2$Br), 2.95 (t, $^3$J(H,H)=7 Hz, 2H; CH$_2$CO). GC-MS: m$^+$=242.0.

Benzyl 3-diethylphosphonopropionate 56.8 mmol of benzyl 3-bromopropionate (13.8 g) and 1.7 eq of triethyl phosphite (16.0 g) are heated to 140° C. with stirring in a distillation apparatus sealed with a gas balloon for pressure equalization. The bromoethane formed during the reaction is distilled out continuously and collected in a receiver flask cooled to 0° C. After 4 h, the remaining oily residue is fractionally distilled under high vacuum through a Vigreux column; the product is a colourless oil.

Yield: 12.1 g (40.3 mmol, 71%), slightly impure, R$_f$=0.33 (A:H 2:3).

For greater purity, the product can be purified where appropriate by flash chromatography (eluent A:H 2:3).

NMR (CDCl$_3$): $^1$H (250 MHz): δ=7.31 (s, 5H; H ar), 5.10 (s, 2H, CH$_2$—OCO), 4.05 (m, 4H; CH$_2$OP), 2.61 (m, 2H; CH$_2$CO), 2.04 (m, 2H; CH$_2$P), 1.26 (t, $^3$J(H,H)=7 Hz, 6H; CH$_3$). $^{31}$P (101.256 MHz): δ=28.5 (s) GC-MS: m$^+$=300.0.

3-Diethylphosphonopropionic Acid 40.3 mmol of benzyl 3-diethylphosphonopropionate (12.1 g) are dissolved in 100 ml of ethanol, and 2 g of catalyst (5% Pd/C) are added. After stirring under an H$_2$ atmosphere for 4 h, the active carbon is filtered off, and the solvent is distilled out. The product results as a colourless oil which slowly solidifies to a colourless solid at room temperature. The product is slightly contaminated with ethyl 3-diethylphosphonopropionate which, where appropriate, can be transferred into the organic phase by shaking several times with water and hexane, and be removed.

Yield: 8.2 g (39.0 mmol, 97%). NMR (CDCl$_3$): $^1$H (250 MHz): δ=10.60 (bs, 1H; COOH), 4.07 (m, 4H; CH$_2$O), 2.59 (m, 2H; CH$_2$CO), 2.06 (m, 2H; CH$_2$P), 1.29 (t, $^3$J(H,H)=7 Hz, 6H; CH$_3$) $^{13}$C (62.896 MHz): δ=174.5 (d, J(C,P)=18.5 Hz; COOH), 62.1 (d, J(C,P)=6.6 Hz; CH$_2$—O), 27.1 (d, J(C,P)=3.8 Hz; CH$_2$—COOH), 2.07 (d, J(C,P)=144.9 Hz; CH$_2$—P), 16.2 (d, J(C,P)=6.1 Hz; CH$_3$). $^{31}$P (101.256 MHz): δ=29.5 (s).

Analytical Data for the Cyclopeptides with Phosphonate Linker

EXAMPLE 4

2 Aminohexanoic Acids in the Spacer

Cyclo-(Arg-Gly-Asp-DPhe-Lys (N$^\epsilon$H[CO—(CH$_2$)$_5$—NH]$_2$-Lys-[Lys-(CO—CH$_2$—CH$_2$—PO$_3$H$_2$)$_2$]$_2$))

MS (ESI): m/z (%): 1756.9 (100) [m–H$^+$], 1778.8 (48) [m+Na$^+$–2H$^+$], 1794.9 (18) [m+K$^+$–2H$^+$]. NMR ([D$_6$]DMSO): $^{31}$p (101.256 MHz): δ=29.63 (s, 1P), 29.59 (s, 1P) 29.57 (s, 1P), 29.38 (s, 1P).

EXAMPLE 5

3 Aminohexanoic Acids in the Spacer

Cyclo-(Arg-Gly-Asp-DPhe-Lys (N$^\epsilon$H—[CO—(CH$_2$)$_5$—NH]$_3$-Lys-[Lys-(CO—CH$_2$—CH$_2$—PO$_3$H$_2$)$_2$]$_2$)

MS (ESI): m/z (%): 934.9 (100) [m–2H$^+$], 1870.0 (27) [m–H$^+$]. NMR ([D$_6$]DMSO): $^{31}$p (101.256 MHz): δ=29.57 (s, 1P), 29.51 (s, 2P), 29.33 (s, 1P).

EXAMPLE 6

2 Heptaethylene Glycol Amino Carboxylic Acids in the Spacer

Cyclo-(Arg-Gly-Asp-DPhe-Lys (N$^\epsilon$H—[CO—CH$_2$(—O—CH$_2$CH$_2$)$_6$—NH]$_2$-Lys-[Lys-(CO—CH$_2$—CH$_2$—PO$_3$H$_2$)$_2$]$_2$))

MS (ESI): m/z (%): 1086.4 (100) [m–2H$^+$], 1097.7 (73) [m+Na$^+$–3H$^+$]NMR ([D$_6$]DMSO): $^{31}$p (101.256 MHz): δ=29.66 (s, 1P), 29.61 (s, 1P), 29.59 (s, 1P), 29.45 (s, 1P).

In addition, all the aforementioned peptides were characterized by $^1$H NMR spectroscopy (250 MHz), and the expected spectra were obtained.

EXAMPLE 7

Ti or TiAl$_6$V$_4$ shaped articles with a diameter of 10 mm and a height of 1-2 mm are precleaned in distilled water at 60° C.

in an ultrasonic bath for 15 min, then washed with acetone for 30 min and then twice with distilled water, and dried in a drying oven for eight hours.

The shaped articles are transferred into 48 wells (Costar, "non-tissue culture treated" Art. No. 3574). To attach the bioactive, cell adhesion-mediating molecules B (where B can be a cyclopeptide, peptide mimetic or linear peptide according to claim 2) to the prepared shaped articles, molecule B-containing stock solutions ("B solutions") are prepared in a final concentration of 1 mM in one of the aqueous buffers Tris-HCl (10 mM, pH 8.7), Tris-HClO$_4$ (10 mM, pH 8.7) or PBS, pH 7.4. Concentration series with the "B solutions" final concentrations of in each case 1 nm, 10 nm, 100 nm, 1 μm, 10 μm and 100 μm are then prepared by dilution with PBS, pH 7.4. The shaped articles are each covered with 250 μl of the respective B solution and then incubated at room temperature for 18-24 hours. To remove unbound B molecules, the samples are washed three times with PBS, pH 7.4, and stored in PBS, pH 7.4, at 4° C. overnight.

Nonspecific cell binding sites are blocked by adding 250 μl of a 5% BSA (bovine serum albumine) solution, pH 7.4, to each shaped article, then incubating at room temperature for 2 hours and washing once with PBS, pH 7.4.

Ti and TiAl$_6$V$_4$ shaped articles which are treated with corresponding buffer solutions (Tris-HCl 10 mM, pH 8.7; Tris-HClO$_4$ 10 mM, pH 8.7; PBS, pH 7.4) instead of B solutions serve as negative controls.

The extent of the resulting coatings on the shaped articles is assessed by analysis, and the biological activity is determined in vitro by means of a cell adhesion test.

EXAMPLE 8

Ivory shaped articles as model of a natural bone substitute material with a diameter of 10 mm and a height of 100 μm are produced by cutting out cylinders with a diameter of 10 mm and subsequently sawing to a thickness of 100 μm in a Buehler ISOMET low speed saw. The samples are then cleaned in distilled water at 60° C. in an ultrasonic bath for 10 min and thereafter washed twice with distilled water and dried in a drying oven for 8 hours.

The procedure for coating the shaped articles with B solutions is as described in example 7.

The extent of the resulting coating on the shaped articles is assessed by analysis, and the biological activity is determined in vitro by means of a cell adhesion test.

EXAMPLE 9

Shaped articles of the commercially available bone substitute material Endobon® (from Biomet Merck, Germany) with a diameter of 10 mm and a height of 100 μm are produced by cutting out cylinders with a diameter of 10 mm and subsequently sawing to a thickness of 100 μm in a Buehler ISOMET low speed saw. The samples are then cleaned in distilled water at 60° C. in an ultrasonic bath for 10 min and thereafter washed twice with distilled water and dried in a drying oven for 8 hours.

The procedure for coating the shaped articles with B solutions is as described in example 7.

The extent of the resulting coating on the shaped articles is assessed by analysis, and the biological activity is determined in vitro by means of a cell adhesion test.

Example for Cell Adhesion Test

The adhesion of mouse MC3T3 H1 osteoblast cultures in vitro to RGD-peptide-coated material surfaces was investigated. In this test, 50 000 cells/cm$^2$ were inoculated and, after incubation in serum-free medium at 37° C./95% atmospheric humidity for one hour, the proportion of adhered cells was determined.

Cell adhesion rate [%]=adhered cells/inoculated cells×100

Peptide: cell adhesion rate [%]
Cyclo-(Arg-Gly-Asp-DPhe-Lys (N$^\varepsilon$H-[CO—(CH$_2$)$_5$—NH]$_2$-Lys-[Lys-(CO—CH$_2$—CH$_2$—PO$_3$H$_2$)$_2$]$_2$):75
Cyclo-(Arg-Gly-Asp-DPhe-Lys (N$^\varepsilon$H-[CO—(CH$_2$)$_5$—NH]$_3$-Lys-[Lys-(CO—CH$_2$—CH$_2$—PO$_3$H$_2$)$_2$]$_2$)):62

---

We claim:

1. A compound of formula I

B-Q-X$_1$         1 wherein

B is a bioactive, integrin-binding molecule which is, (1) cyclo-(Arg-Gly-Asp-Z$_1$) (iv), wherein Z$_1$ is, in each case independently of one another, an amino acid radical or a di- or tripeptide residue, wherein the amino acid(s) are selected independently of one another, from Ala, Asn, Asp, Arg, Cys, Gln, Glu, Gly, His, homo-Phe, Ile, Leu, Lys, Met, Orn, Phe, Phg, Pro, Ser, Thr, Trp, Tyr, and Val;

(v)

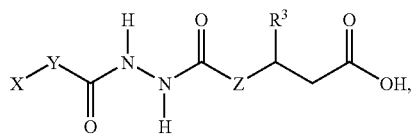

(2) wherein

X is H$_2$N—C(=NH)—NH, Het-NH—, H$_2$N—C(=NH)—, A-C(=NH)—NH— or Het-,

Y is —(CH$_2$)$_n$—,

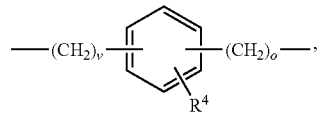

(CH$_2$)$_s$—CH(R$^4$)—(CH$_2$)$_t$— or (CH$_2$)$_p$-Het$^1$-(CH$_2$)$_q$—,

Z is N—R$^2$ or CH—R$^2$,

R$^2$ is H or alkyl having 1 to 4 carbon atoms,

R$^3$ is H, Ar, Het or A,

R$^4$ is H, A, Ar, OH, OA, OAr, arylalkyl, Hal, CN, NO$_2$, CF$_3$ or OCF$_3$,

A is COOH, NH$_2$ or alkyl having 1-6 carbon atoms, which is unsubstituted or substituted by COOH or NH$_2$, Ar is phenyl, which is unsubstituted or mono-, di- or trisubstituted by A, OH, OA, CF$_3$, OCF$_3$, CN, NO$_2$ or Hal, and which is optionally substituted by phenyl, which is mono-, di- or trisubstituted by A, OH, OA, NH$_2$, OCF$_3$, CN, NO$_2$ or Hal in such a way as to give unsubstituted or substituted biphenyl, Hal is F, Cl, Br or I, Het is a saturated or partially or fully unsaturated mono- or bicyclic heterocyclic radical having 5 to 10 ring members, 1 to 3 N atoms and/or 1 S or O atom(s) and the heterocyclic radical can be mono- or disubstituted by CN, Hal, OH, NH$_2$, COOH, OA, CF$_3$, A, NO$_2$, Ar or OCF$_3$, Het$^1$ is a 5- or 6-membered aromatic heterocycle having 1 to 4 N and/or S atoms, which is optionally unsubstituted or mono- or disubstituted by F, Cl, Br, A, OA or OCF$_3$, n is 4, 5 or 6, m, o, p, and q are, each independently, 0, 1 or 2, s, and t are, each independently, 0, 1, 2, 3, 4 or 5;

(3) Thr-Trp-Tyr-Lys-Ile-Ala-Phe-Gln-Arg-Asn-Arg-Lys (vi), (SEQ. ID. NO. 1);

(4) Trp-Tyr-Lys-Ile-Ala-Phe-Gln-Arg-Asn-Arg-Lys (vii), (SEQ. ID. NO. 2);

(5) Tyr-Lys-Ile-Ala-Phe-Gln-Arg-Asn-Arg-Lys (viii), (SEQ. ID. NO. 3);

(6) Thr-Trp-Tyr-Lys-Ile-Ala-Phe-Gln-Arg-Asn-Arg (ix), (SEQ. ID. NO. 4);

(7) Thr-Trp-Tyr-Lys-Ile-Ala-Phe-Gln-Arg-Asn (x), (SEQ. ID. NO. 5); or (8) Thr-Trp-Tyr-Lys-Ile-Ala-Phe-Gln-Arg (xi), (SEQ. ID. NO. 6);

Q is absent or is an organic spacer molecule which is $[CO-(CH_2)_x-NH-]_m$ (xii)

$[CO-CH_2(-O-CH_2CH_2)_y-]_m$ (xiii)

$[CO-(CH_2)_z-CO-]$ (xiv)

$[NH-(CH_2)_z-NH-]$ (xv)

$[CO-CH_2-(OCH_2CH_2)_y-O-CH_2-CO-]$ (xvi) or $[NH-CH_2CH_2-(OCH_2CH_2)_y-NH-]$ (xvii)

or a combination thereof, wherein m in each case independently of one another is 1-20, x is 1-12, y is 1-50, and z is 1-12, and X$_1$ is an anchor molecule, which is -Lys-(CO-CH$_2$-(CH$_2$)$_n$-(PO$_3$H$_2$)$_2$ (i)

-Lys-[Lys-(CO-CH$_2$-(CH$_2$)$_n$-PO$_3$H$_2$)$_2$]$_2$ (ii) or

-Lys-(Lys[-Lys-(CO-CH$_2$-(CH$_2$)$_n$-PO$_3$H$_2$)$_2$]$_2$ (iii), wherein n, in each case independently of one another, is 0, 1, 2 or 3, and wherein a free amino group in group B is linked in a peptide-like manner to a free carboxyl group in group Q or in group X$_1$, or a free amino group of the group Q is linked in a peptide-like manner to a free carboxyl group of the radical X$_1$, or a salt thereof or a stereoisomer thereof.

2. A compound according to claim 1, wherein Q is $[CO-(CH_2)_x-NH-]_m$ (xviii)

$[CO-CH_2(-O-CH_2CH_2)_y-NH-]_m$ (xix)

$[CO-(CH_2)_z-CO-]$ (xx)

$[NH-(CH_2)_z-NH-]$ (xxi)

$[CO-CH_2-(OCH_2CH_2)_y-O-CH_2-CO-]$ (xxii) or $[NH-CH_2CH_2-(OCH_2CH_2)_y-NH-]$ (xxiii)

or a combination thereof, wherein m is 1-8, x is 1-5, y is 1-6, and z is 1-6, or a salt thereof or a stereoisomer thereof.

3. A compound according to claim 1 which is a) Cyclo(Arg-Gly-Asp-DPhe-Lys($^\epsilon$NH-[CO-(CH$_2$)$_5$-NH]$_2$-Lys-[Lys-(CO-CH$_2$-(CH$_2$)$_n$-PO$_3$H$_2$)$_2$]$_2$));

b) Cyclo(Arg-Gly-Asp-DPhe-Lys($^\epsilon$NH-[CO-(CH$_2$)$_5$-NH]$_3$-Lys-[Lys-(CO-CH$_2$-(CH$_2$)$_n$-PO$_3$H$_2$)$_2$]$_2$; or c) Cyclo(Arg-Gly-Asp-DPhe-Lys($^\epsilon$NH-[CO-CH$_2$(-O-CH$_2$CH$_2$)$_6$-NH]$_2$-Lys-[Lys-(CO-CH$_2$-(CH$_2$)$_n$-PO$_3$H$_2$)$_2$]$_2$));

wherein n is 1.

4. A medicament which comprises a compound of Formula I according to claim 1 and a carrier.

5. An implant which is suitable for human and animal organs, consisting of a carrier matrix and a layer of a bioactive, cell adhesion-mediating molecule surrounding said matrix, wherein a surrounding layer comprises a compound of Formula I according to claim 1, and wherein said carrier matrix and said compound of Formula I are bound via an ionic or adsorptive bond.

6. An implant according to claim 5, wherein the carrier matrix and/or a surface thereof is a metal or a metal oxide.

7. An implant according to claim 5, wherein the carrier matrix and/or a surface thereof is a bone or tooth substitute material.

8. An implant according to claim 7, wherein the bone or tooth substitute material consists of calcium phosphate mixtures.

9. A process for the preparation of a compound according to claim 1 comprising linking, in a peptide-like manner, a bioactive molecule B optionally comprising a protective group with a spacer-anchor molecule (Q-X$_1$) or an anchor molecule (X$_1$), wherein said Q-X$_1$ and said X$_1$ groups comprise one or more protective groups;

removing said protective groups; and optionally converting a basic or acidic compound of Formula I to a salt thereof by treating with an acid or base.

10. A method of treating a disorder, defect or inflammation caused by implants, comprising administering to a subject in need thereof, a compound according to claim 1.

11. A method for the treatment of an osteolytic disorder, thrombosis, cardiac infarct, or arteriosclerosis, comprising administering to a subject in need thereof, a compound according to claim 1.

12. A method for the acceleration and strengthening of the integration process of the implant or of the biocompatible surface into the tissue, comprising administering to a subject in need thereof, a compound according to claim 1.

* * * * *

UNITED STATES PATENT AND TRADEMARK OFFICE
CERTIFICATE OF CORRECTION

PATENT NO.       : 7,655,624 B2                                        Page 1 of 1
APPLICATION NO.  : 10/344669
DATED            : February 2, 2010
INVENTOR(S)      : Meyer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1816 days.

Signed and Sealed this

Twenty-third Day of November, 2010

David J. Kappos
*Director of the United States Patent and Trademark Office*